(12) United States Patent
Al-Balkhi et al.

(10) Patent No.: US 9,370,407 B1
(45) Date of Patent: Jun. 21, 2016

(54) CANINE TOOTH TRACTION DEVICE AND METHOD

(71) Applicant: KING SAUD UNIVERSITY, Riyadh (SA)

(72) Inventors: Khalid M. Al-Balkhi, Riyadh (SA); Sahar Faisal Al-Barakati, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 14/644,102

(22) Filed: Mar. 10, 2015

(51) Int. Cl.
  *A61C 3/00* (2006.01)
  *A61C 7/20* (2006.01)
  *A61C 7/18* (2006.01)
  *A61C 7/12* (2006.01)

(52) U.S. Cl.
  CPC . *A61C 7/20* (2013.01); *A61C 7/125* (2013.01); *A61C 7/18* (2013.01)

(58) Field of Classification Search
  CPC .............. A61C 7/00; A61C 7/10; A61C 7/18; A61C 7/20; A61C 7/22; A61C 7/28; A61C 7/125; A61C 7/282
  USPC .......................................... 433/18, 20, 21, 24
  See application file for complete search history.

(56) References Cited

U.S. PATENT DOCUMENTS

| | | | | |
|---|---|---|---|---|
| 4,187,610 A | * | 2/1980 | Ziegler | 433/24 |
| 4,479,779 A | * | 10/1984 | Wool | 433/20 |
| 4,731,018 A | * | 3/1988 | Adell | 433/20 |
| 4,892,479 A | * | 1/1990 | McKenna | 433/20 |
| 5,064,370 A | * | 11/1991 | Jones | 433/21 |
| 5,112,221 A | * | 5/1992 | Terry | 433/21 |
| 5,292,249 A | | 3/1994 | German | |
| 5,334,015 A | * | 8/1994 | Blechman | 433/18 |
| 5,984,675 A | * | 11/1999 | White | 433/21 |
| 6,120,289 A | * | 9/2000 | Cleary et al. | 433/22 |
| 6,431,861 B1 | * | 8/2002 | White | 433/20 |
| 2005/0064359 A1 | * | 3/2005 | Nikodem | 433/18 |
| 2007/0264607 A1 | | 11/2007 | Olavarria Landa | |
| 2008/0182219 A1 | | 7/2008 | Spalty | |
| 2011/0014583 A1 | * | 1/2011 | Romano et al. | 433/10 |

* cited by examiner

*Primary Examiner* — Matthew Nelson
(74) *Attorney, Agent, or Firm* — Richard C. Litman

(57) ABSTRACT

The canine tooth traction device is a 0.019"×0.025" stainless steel sectional wire. It is distally inserted in the molar band of a transpalatal arch anchorage and mesially ligated to a bondable attachment (bracket or button) on the canine tooth. The canine tooth traction device is an elongated member that has a cinching end and an attachment end. The cinching end is 15 mm in length, with 4-5 mm length activation bend of 45° mesial to the molar band. The length of the traction arm from the activation bend to the bondable attachment ligating loop is 40-50 mm. The loop of the attachment end is ligated to the bracket or button. The cinching end is cinched toward and behind the anchor headgear molar tube.

8 Claims, 4 Drawing Sheets

CANINE TOOTH TRACTION DEVICE AND METHOD

BACKGROUND OF THE INVENTION

1. Field of the Invention

The present invention relates to dental instruments, and particularly to a canine tooth traction device and method.

2. Description of the Related Art

Impacted or unerupted maxillary canines can present challenging clinical problems frequently encountered by orthodontists. Further, these clinical problems may be associated with other types of malocclusion, or may be the sole presenting feature of a malocclusion. Permanent canines have unique functional and esthetic characteristics, so the literature has paid attention to the diagnosis, treatment options, and the development of new canine disimpaction and alignment devices.

Removable appliances have been used for the alignment of impacted canines. Possible disadvantages to these appliances are the inability to provide controlled tooth movement in all planes of space, and the need for patient cooperation. Fixed appliances have also been commonly used as alternatives that can provide good control of tooth movement. Examples of these types of appliances include full fixed appliances with traction force applied via elastic chains running to rigid arch wires.

Separated devices have also been used to extrude the canine by means of a sectional approach. An example of a separated device includes a sectional appliance using rectangular titanium molybdenum wires (TMA, 0.017×0.02") for the alignment of ectopic canines. Another example of a separated device is one that employs a "K-9 spring" using rectangular titanium molybdenum wire (0.017×0.025") to extrude impacted canines. Further separated devices include a modified "K-9 spring" by adding buccal crown torque in the premolar and molar regions.

Even though the use of (0.019×0.025") stainless steel wire provides efficient force, a wide range of activation without deformation, stability without rocking, and the ability to reactivate repeatedly intraorally without removing it, there are possible drawbacks. For example, the activation of such sectional wire can result in strong reciprocal clockwise rotational moment, resulting in distal crown tipping, extraction/intrusion, and rotation of the first molar.

Thus, a canine tooth traction device and method solving the aforementioned problems is desired.

SUMMARY OF THE INVENTION

The canine tooth traction device is used with the molar band of a transpalatal arch anchorage and a bracket that can be mounted onto a canine tooth. The canine tooth traction device is an elongate member that has an attachment end and a fixing end. The elongate member has a bend of 45° in a region between the attachment end and the fixing end. The attachment end is connected to the bracket and the fixing end is fixed to the anchor. The fixing end is cinched towards and behind the anchor.

A method for canine tooth traction includes the step of anchoring an anchor that is configured for use with a molar tooth and setting a bracket configured for use with a canine tooth. Remaining steps of the method include cinching an elongate member that has a 45° bend to the anchor and attaching a remaining end of the elongate member to the bracket.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The canine tooth traction device and method for canine tooth traction allows for an impacted canine tooth, such as a buccally impacted or a palatally impacted canine tooth, to be extruded appropriately in the mouth of a patient. The canine tooth traction device can provide a wide range of activation and a continuous efficient force to move the impacted canine tooth vertically and buccally without rocking in a short time.

Figure 1:
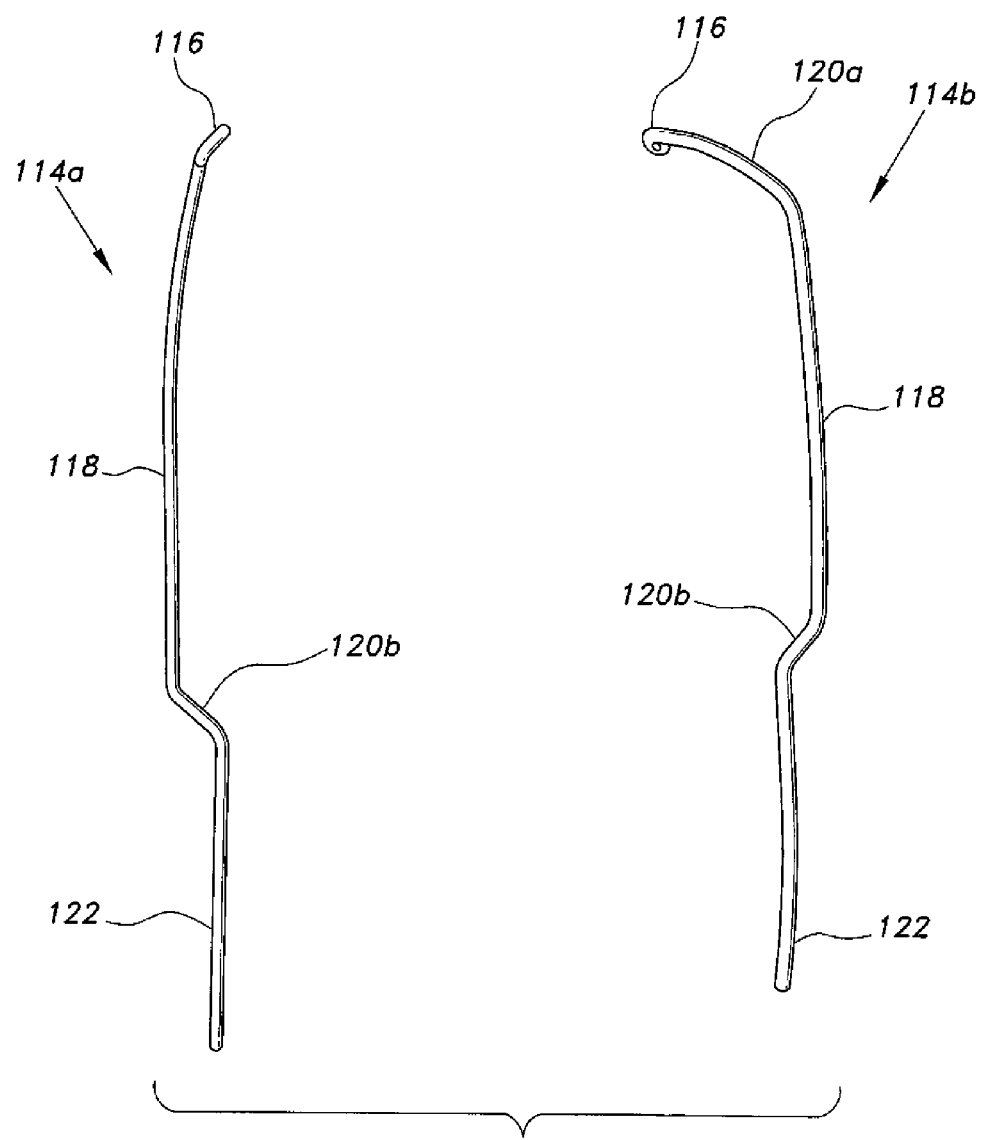
FIG. 1 is an upper view of a kit of canine tooth traction devices according to the present invention, including a buccal elongate member and a palatal elongate member.
Figure 2A:
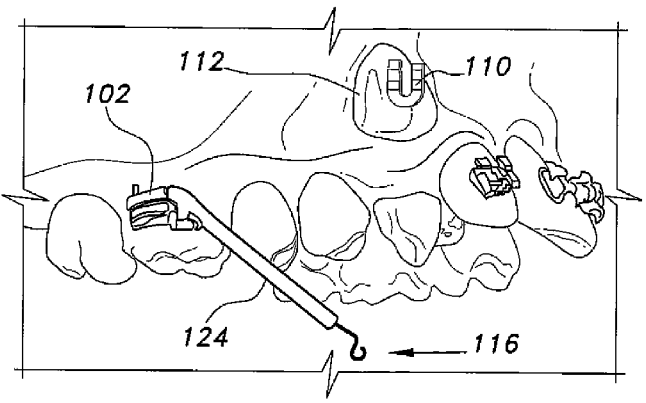
FIG. 2A is an environmental perspective view showing a step in installing a canine tooth traction device according to the present invention, where the attachment end is unattached from a buccally impacted canine tooth.
Figure 2B:
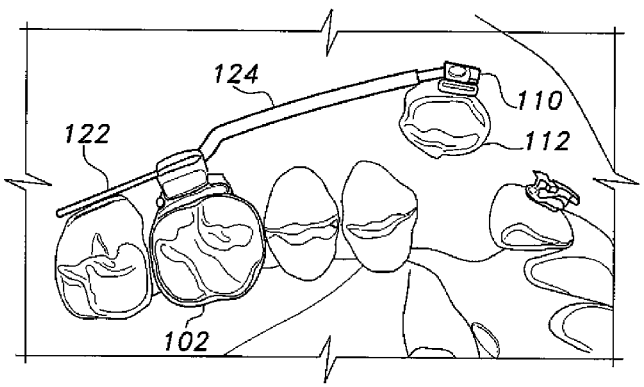
FIG. 2B is an environmental perspective view showing a step in installing a canine tooth traction device according to the present invention, where the attachment end is attached to the buccally impacted canine tooth.
Figure 2C:
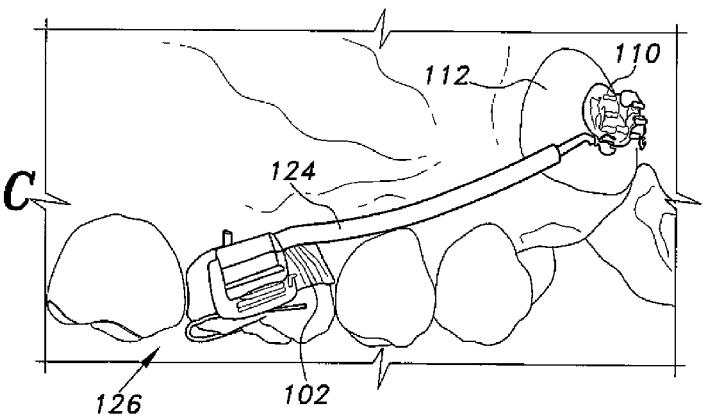
FIG. 2C is an environmental perspective view showing a step in installing a canine tooth traction device according to the present invention for a buccally impacted canine, where the fixing end is cinched around a molar tooth.
Figure 3A:
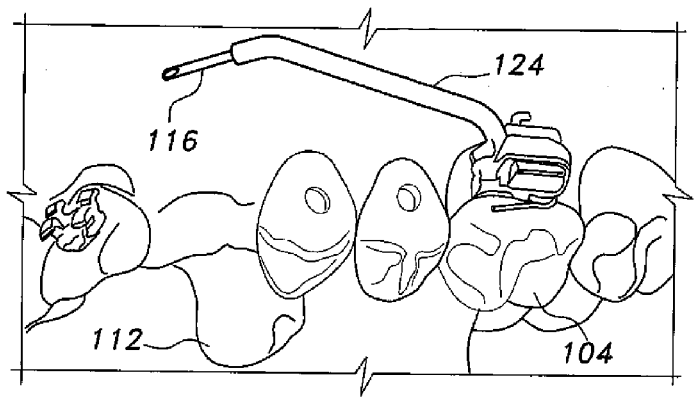
FIG. 3A is an environmental perspective view showing a step in installing a canine tooth traction device according to the present invention for a palatally impacted canine, showing the fixing end cinched around a molar tooth.
Figure 3B:
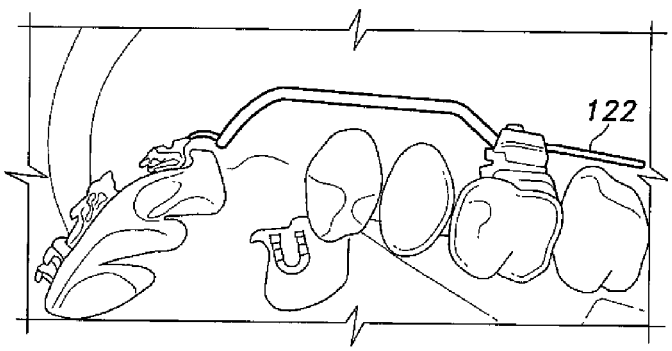
FIG. 3B is an environmental perspective view showing a step in installing a canine tooth traction device according to the present invention for a palatally impacted canine, showing the attachment end unattached from the palatally impacted canine tooth.
Figure 3C:
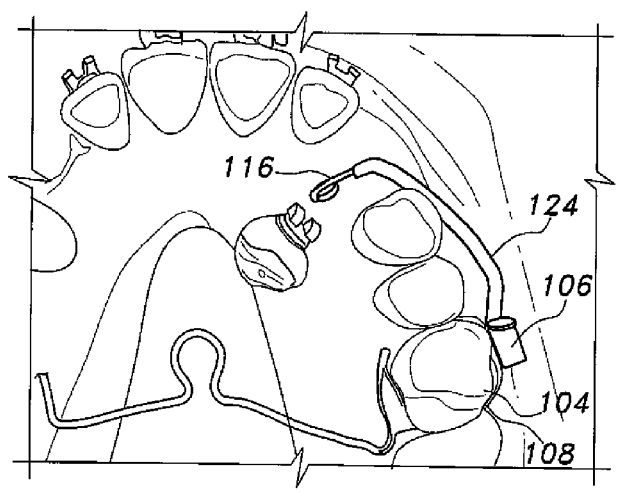
FIG. 3C is an environmental perspective view showing a step in installing a canine tooth traction device according to the present invention for a palatally impacted canine, showing the attachment end being connected to the palatally impacted canine tooth.
Figure 4A:
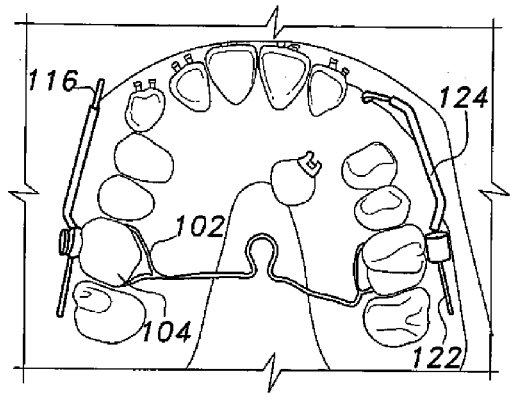
FIG. 4A is an environmental perspective view showing a step in installing canine tooth traction devices according to the present invention, showing both a buccally impacted canine tooth and a palatally impacted canine tooth.
Figure 4B:
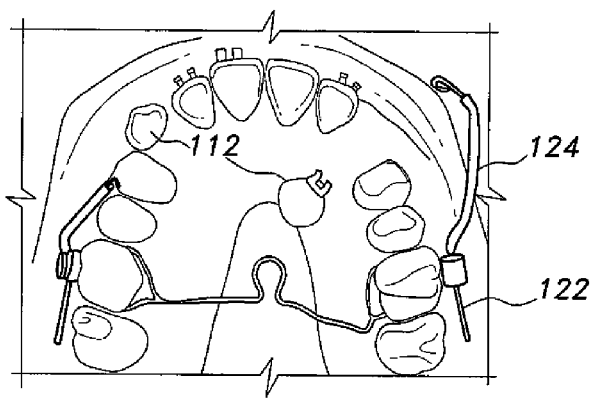
FIG. 4B is an environmental perspective view showing a step in installing canine tooth traction devices according to the present invention, showing both a buccal elongate member unattached from the buccally impacted canine tooth and a palatal elongate member unattached from the palatally impacted canine tooth.
Figure 4C:
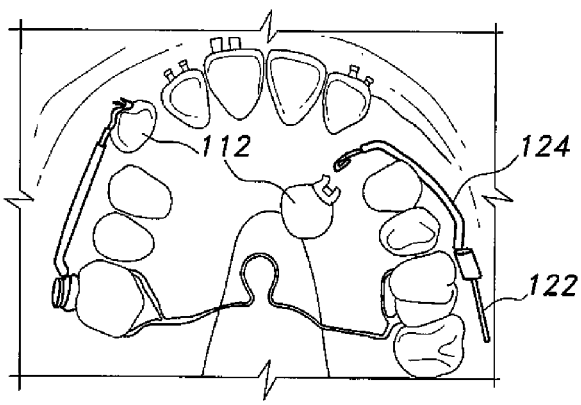
FIG. 4C is an environmental perspective view showing a step in installing canine tooth traction devices according to the present invention, showing the buccal elongate member attached to the buccally impacted canine tooth and the palatal elongate member being attached to the palatally impacted canine tooth.

Referring to FIGS. 1, 2A-2C, 3A-3C, and 4A-4C, a kit 100 of canine tooth traction devices is shown. As shown in FIG. 1, the canine tooth traction device kit 100 can include a buccal elongate member 114a, a palatal elongate member 114b, or both. Both the buccal elongate member 114a and the palatal elongate member 114b can be made from a number of materials found in dentistry. For example, the material can be 0.019×0.025" rectangular stainless steel arch wire. The selection of the buccal elongate member 114a or the palatal elongate member 114b depends upon the patient's needs and the position of the patient's impacted canine tooth. Further, as shown in FIGS. 4A-4C, both the buccal elongate member 114a and the palatal elongate member 114b can be used together if the patient has both a buccally impacted canine and a palatally impacted canine.

Continuing with FIG. 1, both the buccal elongate member 114a and the palatal elongate member 114b have similar features. An attachment end 116 at one end of the elongate member 114a, 114b includes a ligating loop. The attachment end 116 can be connected to a bracket 110 mounted onto a tooth. For example, FIGS. 2A-2C, 3A-3C, and 4A-4C show a bracket 110 mounted onto a canine tooth 112. The bracket 110 includes a hook to accept the attachment end. The attachment end 116 ligates the elongate member 114a,114b to the canine for activation.

The elongate members 114a, 114b also have a mesial buccal arm 118. The mesial buccal arm can have a length in a range of about 40-50 mm. One difference between the buccal elongate member 114a and the palatal elongate member 114b is that the palatal elongate member 114b includes a bend 120a towards the attachment end 116. As seen clearly in FIG. 1, the bend 120a is positioned in a region between the attachment end 116 and the mesial buccal arm 118. The bend 120a is about 45° and allows for palatally impacted canines to be treated. In contrast, the buccal elongate member 114a does not have this bend and instead has a generally straight shape.

The mesial buccal arm 118 can be covered with a sleeve of protective tubing 124 for added patient comfort, as shown in FIGS. 2A-2C, 3A-3C, and 4A-4C. In addition to the mesial buccal arm 118, both elongate members 114a,114b have a fixing end 122. The fixing end forms a distal cinching tag that has a length of about 15 mm. Further, the fixing end 122 is configured to connect to the molar band 102 of a transpalatal arch anchorage (TPA). As shown in FIGS. 2A-2C, 3A-3C, and 4A-4C, the molar band 102 can be mounted onto a molar tooth 104.

As shown in FIG. 3C, the molar band 102 includes an auxiliary tube 106 and a headgear molar tube 108 to allow for the fixing end 122 of the elongate members 114a,114b to be fixed to the molar band 102. The fixing end 122 extends through the auxiliary tube 106 and is cinched 126 mesially behind the headgear molar tube 108 of the molar band 102 of the TPA, as shown in FIGS. 2C and 3C. Cinching the fixing end 122 behind the molar tooth 104 prevents any rotation or rocking of the elongate member 114a,114b during use. Positioned between the mesial buccal arm 118 and the fixing end 122 is an offset activation bent 120b having a length of about 4-5 mm. The offset activation bent 120b keeps the elongate member 114a, 114b buccally away from the gingiva (as well as the bicuspid's brackets), and also acts as a stop during activation.

The initial activation of the elongate member 114a,114b is done extra-orally by holding the wire with a pliers at the "offset activation bent" 120 and moving the "mesial buccal arm" 118 either buccally, or occlusally, or both, according to the direction of the desired canine movement. The amount of activation is generally judgmental and slightly more than the distance of the impacted canine to the final desired position. After insertion of the fixing end 122 into the auxiliary tube 106 of the anchor 102, the fixing end 122 is cinched towards and behind the headgear molar tube 108, gingivally or occlusally, depending on the position of the headgear tube 108 of the molar band 102, if it is gingivally or occlusally positioned, respectively, and all the way mesially with Weingart pliers until the fixing end 122 is behind and mesial to the headgear molar tube 108. The attachment end 116 is then pushed toward the canine 112 and ligated tightly with ligature to the bracket 110, as shown in FIGS. 2A-2C, 3A-3C, and 4A-4C.

Reactivations in the following clinical visits are done intraorally by dc-ligating the attachment end 116 and bend 120 or moving the mesial buccal arm 118 further toward the direction of desired tooth movement, then re-ligating the "ligating loop". Reactivation appointments are recommended between 4-8 week intervals. Removal of the elongate members 114a, 114b is done by holding the fixing end 122 that is positioned mesial to the headgear tube with Weingart pliers and de-cinching all the way distally. Then, with a distal end cutter, cut the fixing end 122. A high-speed short diamond bur with excessive water could also be used to cut the fixing end 122 that is distal to the axially molar tube if the fixing end 122 was bent and difficult to remove through the auxiliary tube.

A 16-year old girl presented with bilateral palatally impacted canines treated with the canine traction device 104b. The pre and post panoramic comparison disclosed that the canines were brought into alignment with the roots well aligned and the path travelled by the impacted canines was about 19 mm.

More specific clinical procedures include the following steps: (1) The maxillary teeth should be leveled, aligned, reaching reasonable rectangular continuous arch wire (0.016×0.022" or 0.017×0.025") and having sufficient space to accommodate the impacted canine. (2) The maxillary continuous arch wire should have upward/gingival step up exactly distal to the lateral incisor bracket and mesial to the bicuspid bracket to hold the canine space during activation. (3) The TPA anchor 102 should be set before initiating the use of the elongate member 114a,114b, to control the reciprocal force and moment resulting from the activation. (4) Once the impacted canine is surgically exposed (opened or closed approach), it should be bonded with an attachment (button, bracket, eyelet, cleat or section of gold chain). (5) Ten days after the surgical exposure (the start of soft tissue healing, yet no bone formation), the elongate member 114a,114b is bent and activated extra-orally, then placed in the molar auxiliary tube 106. The fixing end 122 is cinched underneath the headgear molar tube 108 and the attachment end 116 is ligated to the bonded attachment of the impacted canine. (6) Follow-up clinical visits should be done between 4-8 week intervals, and reactivations of the sectional is done intraorally by de-ligating the attachment end 116, adjustment/activation of the elongate member 114a,114b, and then re-ligating it again. (7) It may take 1-3 clinical visits to extrude the impacted canine to the desired position depending on the difficulty and/or the original position of the impacted canine. (8) Overcoming occlusal interferences during the extrusion of palatally impacted canines can be accomplished by either altering the direction of the sectional traction or by opening the bite temporally with posterior bite plane or posterior occlusal composite.

It is to be understood that the present invention is not limited to the embodiments described above, but encompasses any and all embodiments within the scope of the following claims.

We claim:
1. A canine tooth traction device kit, comprising:
   a buccal elongate member made from wire, the buccal elongate member having a generally straight configuration and consisting of:

an attachment end having a ligating loop formed therein for ligating the attachment end to a bracket mounted on a buccally impacted canine tooth;
a fixing end opposite the attachment end, the fixing end forming a distal cinching tag having a length of about 15 mm;
a mesial buccal arm disposed between the attachment end and the fixing end; and
an offset activation bend sloping at an angle between the fixing end and the mesial buccal arm;
wherein the loop at the attachment end is adapted for ligation to the bracket on the buccally impacted canine tooth, the buccal elongate member being adapted for insertion through an auxiliary tube and the distal cinching tag being adapted for cinching behind a headgear tube of a transpalatal arch anchorage in order to apply traction to the buccally impacted canine tooth; and
a palatal elongate member, the palatal elongate member consisting of:
an attachment end having a ligating loop formed therein for ligating the attachment end to a bracket mounted on a palatally impacted canine tooth;
a fixing end opposite the attachment end of the palatal elongate member, the fixing end forming a distal cinching tag;
a mesial buccal generally straight arm disposed between the attachment end and the fixing end of the palatal elongate member;
a bend of about 45° formed in the palatal elongate member between the mesial buccal arm and the attachment end of the palatal elongate member, wherein the bend is angled toward the attachment end; and
an offset activation bend sloping at an angle between the fixing end and the mesial buccal arm of the palatal elongate member;
wherein the loop at the attachment end of the palatal elongate member is adapted for ligation to the bracket on the palatally impacted canine tooth, the palatal elongate member being adapted for insertion through an auxiliary tube and the distal cinching tag being adapted for cinching behind a headgear tube of a molar band of the transpalatal arch anchorage in order to apply fraction to the palatally impacted canine tooth.

2. The canine tooth traction device kit according to claim 1, further comprising a sleeve of protective tubing disposed around the mesial buccal arm of each elongate member for protecting a patient's cheek intraorally.

3. The canine tooth traction device kit according to claim 1, wherein each said elongate member is made from rectangular stainless steel arch wire and has a rectangular cross-sectional dimension of about 0.019×0.025".

4. A method for applying traction to a canine tooth to align the canine tooth in a patient's mouth, comprising the steps of:
installing a transpalatal arch anchorage (TPA) in the patient's mouth, the TPA having molar bands mounted on the patient's molars and an auxiliary tube and a headgear tube mounted on each of the molar bands;
bonding a bracket to the canine tooth to be aligned, the bracket having a hook;
providing a traction device kit, comprising:
a buccal elongate member, the buccal elongate member having a generally straight configuration and consisting of:
an attachment end having a ligating loop formed therein for ligating the attachment end to a bracket mounted on a buccally impacted canine tooth;
a fixing end opposite the attachment end, the fixing end forming a distal cinching tag having a length of about 15 mm;
a mesial buccal generally straight arm disposed between the attachment end and the fixing end; and
an offset activation bend sloping at an angle between the fixing end and the mesial buccal arm; and
a palatal elongate member made from wire, the palatal elongate member consisting of:
an attachment end having a ligating loop formed therein for ligating the attachment end to a bracket mounted on a palatally impacted canine tooth;
a fixing end opposite the attachment end of the palatal elongate member, the fixing end forming a distal cinching tag;
a mesial buccal generally straight arm disposed between the attachment end and the fixing end of the palatal elongate member;
a bend of about 45° formed in the palatal elongate member between the mesial buccal arm and the attachment end of the palatal elongate member, wherein the bend is angled toward the attachment end; and
an offset activation bend sloping at an angle between the fixing end and the mesial buccal arm of the palatal elongate member;
selecting at least one of the buccal and palatal elongate members;
holding the selected elongate member with pliers at the offset activation bend between the fixing end and the mesial buccal arm;
bending the mesial buccal arm buccally or occlusally according to the desired direction of canine tooth movement in order to activate the selected elongate member;
inserting the fixing end of the selected elongate member through the auxiliary tube on the molar band;
cinching a distal cinch tag defined by the fixing end behind and mesial to the headgear tube of the molar band using Weingart pliers in order to anchor the fixing end to one of the molars; and
tightly ligating a loop formed in an attachment end of the selected elongate member opposite the fixing end to the hook on the bracket bonded to the canine tooth in order to apply traction to the canine tooth.

5. The method for applying traction to a canine tooth according to claim 4, wherein the canine tooth is buccally impacted.

6. The method for applying traction to a canine tooth according to claim 4, wherein the canine tooth is palatally impacted.

7. The canine tooth traction device according to claim 1, wherein the mesial buccal arm of the buccal and palatal elongate members has a length of about 40-50 mm.

8. The canine tooth traction device according to claim 1, wherein the offset activation bend of the buccal and palatal elongate members has a length of about 4-5 mm.

* * * * *